United States Patent [19]
Lashinski et al.

[11] Patent Number: 5,810,868
[45] Date of Patent: Sep. 22, 1998

[54] STENT FOR IMPROVED TRANSLUMINAL DEPLOYMENT

[75] Inventors: Robert Lashinski, Windsor; Matthew Birdsall, Santa Rosa, both of Calif.

[73] Assignee: Arterial Vascular Engineering, Inc., Santa Rosa, Calif.

[21] Appl. No.: 568,834

[22] Filed: Dec. 7, 1995

[51] Int. Cl.$^6$ .................................................. A61M 29/00
[52] U.S. Cl. ........................................... 606/194; 606/198
[58] Field of Search .................................... 606/198, 191, 606/194, 108, 153; 623/1, 12

[56] References Cited

U.S. PATENT DOCUMENTS 5,135,536  8/1992  Hillstead ..................................... 623/1
5,282,824  2/1994  Gianturco ................................. 606/198

*Primary Examiner*—Michael Buiz
*Assistant Examiner*—Kevin Truong
*Attorney, Agent, or Firm*—Richard L. Klein

[57] ABSTRACT

A stent and method for manufacturing a stent comprising an expandable, generally tubular body portion in which one or both ends of the stent are provided with a generally rounded, smooth radiused portion that forms a bulbous protrusion out of the plane of the circumference of the stent. The design of the stent increases the profile of the end of the stent and decreases the risk of injury or vessel dissection during stent deployment.

23 Claims, 6 Drawing Sheets

STENT FOR IMPROVED TRANSLUMINAL DEPLOYMENT

FIELD OF THE INVENTION

This invention relates to medical implant devices. More specifically, the invention relates to an improved implantable stent apparatus for the treatment of stenoses in coronary or peripheral vessels in humans.

BACKGROUND OF THE INVENTION

Cardiovascular disease, including atherosclerosis, is the leading cause of death in the United States. The medical community has developed a number of methods and devices for treating coronary heart disease, some of which are specifically designed to treat the complications resulting from atherosclerosis and other forms of coronary artery narrowing.

An important development for treating atherosclerosis and other forms of coronary narrowing is percutaneous transluminal coronary angioplasty, hereinafter referred to as "angioplasty" or "PTCA". The objective in angioplasty is to enlarge the lumen of the affected coronary artery by radial hydraulic expansion. The procedure is accomplished by inflating a balloon within the narrowed lumen of the coronary artery. Radial expansion of the coronary artery occurs in several different dimensions, and is related to the nature of the plaque. Soft, fatty plaque deposits are flattened by the balloon, while hardened deposits are cracked and split to enlarge the lumen. The wall of the artery itself is also stretched when the balloon is inflated.

Unfortunately, while the affected artery can be enlarged, in some instances the vessel restenoses chronically, or closes down acutely, negating the positive effect of the angioplasty procedure. In the past, such restenosis has frequently necessitated repeat PTCA or open heart surgery. While such restenosis does not occur in the majority of cases, it occurs frequently enough that such complications comprise a significant percentage of the overall failures of the PTCA procedure, for example, twenty-five to thirty-five percent of such failures.

To lessen the risk of restenosis, various devices have been proposed for mechanically keeping the affected vessel open after completion of the angioplasty procedure. Such endoprostheses (generally referred to as "stents"), are typically inserted into the vessel, positioned across the lesion or stenosis, and then expanded to keep the passageway clear. The stent overcomes the natural tendency of the vessel walls of some patients to restenose, thus maintaining the patency of the vessel.

Various types of stents are currently under development, although to date none has proven completely satisfactory during testing. U.S. Pat. No. 4,655,771 to Wallsten describes a stent comprising a tube of stainless wire braid. During insertion, the tube is positioned along a delivery device, such as a catheter, in extended form, making the tube diameter as small as possible. When the stent is positioned across the lesion, it is expanded, causing the length of the tube to contract and the diameter to expand. Depending on the materials used in construction of the stent, the tube maintains the new shape either through mechanical force or otherwise.

U.S. Pat. No. 4,733,665 to Palmaz describes a stent comprising a slotted stainless steel cylinder that forms a mesh when expanded. The stent is delivered to an affected area by a balloon catheter, and is then expanded to the proper size by inflating the balloon.

Stents are typically delivered to affected areas of vessels using standard catheterization techniques. A thin walled hollow guiding catheter is introduced into the body via a relatively large vessel, such as the femoral artery in the groin area or the brachial artery in the arm by insertion through a hollow sheath. The guiding catheter is maneuvered through an approximately 180 degree turn through the aortic arch to descend into the aortic cusp where entry may be gained to either the left or the right coronary artery, as desired.

A flexible guidewire is inserted into the guiding catheter and advanced to the area to be treated. The guidewire is advanced across the lesion in preparation for the advancement of a catheter across the guide wire. Typically a balloon catheter carrying the stent is then introduced over the guidewire to the area to be treated. Radiopaque markers in the balloon segment of the catheter facilitate positioning across the lesion. The balloon catheter is then inflated with contrast material to permit fluoroscopic viewing during treatment. The balloon is inflated until the lumen of the artery is satisfactorily enlarged and the stent is in place.

During delivery of the stent, the stent and balloon catheter must navigate narrow tortuous vessels into the site of a stenosis. Typically, the balloon and stent are covered with a sheath during delivery. Such sheaths facilitate delivery of stents because the sheath prevents the stent from being dislodged from the delivery device. However, sheaths increase the cross-sectional profile of the stent, necessitating use of a guiding catheter with a larger internal diameter. The large diameter of the guiding catheter may increase the risk of complications at the patient access site. Moreover, the larger cross-sectional profile of the stent delivery system may decrease the ability to deliver contrast material through the guiding catheter to enable precise positioning. More important, an increased cross-sectional profile may make it impossible to deliver a stent through narrow and tortuous vessels to the area desired to be treated.

Stent delivery systems without sheaths have been proposed. For example, the Boneau stent described in U.S. Pat. No. 5,292,531 has been used with a modified delivery device described in co-pending U.S. patent application No. 08/451, 270 which is hereby incorporated by reference. The disclosed delivery system secures the stent on the outside of the balloon without the need for a sheath.

However, attempts to deliver expandable stents without using a delivery sheath have resulted in a number of problems. First the relatively rigid stent may be dislodged from the more pliable balloon material of the flexible delivery device when contact occurs between the vessel wall and the stent, particularly during passage through a curve. Additionally, the low mass of the rigid stents, and construction methods of some stents, causes the end portions to have small cross-sections and to be somewhat ridged and sharp. The small, sharp, cross-sections at the ends of the stents increase the risk that a stent will penetrate the vessel wall, particularly when the narrow, rigid end of a stent encounters a curve in a vessel. The flexible delivery device and balloon material follow the contours of the vessel, and when negotiating a curve, the distal end of the more rigid stent may separate slightly from the balloon and delivery device. The separated, sharp distal end may cause abrasion or penetrate the soft tissues of the vessel wall.

These and other complications have resulted in a low level of acceptance for such stents within the medical community for certain procedures, and to date stents have not been accepted as a practical method for treating many chronic restenosis conditions.

It would therefore be desirable to provide methods and apparatus, useful for treating chronic restenosis conditions, that enable delivery of a stent without a sheath and which reduce the risk of vessel abrasion and dissection during delivery.

SUMMARY OF THE INVENTION

In view of the foregoing, it is an object of this invention to provide methods and apparatus, useful for treating chronic restenosis conditions, that enable delivery of a stent without a sheath and which reduce the risk of vessel abrasion and dissection during delivery.

A stent constructed in accordance with this invention may be in the form of an expandable, generally tubular body portion having two ends, wherein at least one end of the stent is provided with a generally rounded, smooth radius.

The deployment methods for implanting a stent constructed in accordance with the present invention include balloon expansion, self-expansion, self-retraction and mechanical expansion. Some of the intended uses include PTCA type stenting, PTA type stenting, graft support, graft delivery, INR use, GI tract use, drug delivery, and biliary stenting.

DETAILED DESCRIPTION OF THE INVENTION

In overview, an endoprosthesis constructed in accordance with the present invention comprises an expandable, generally tubular body portion having two ends. In accordance with the present invention, at least one end of the stent is provided with a generally rounded, smooth radiused portion that forms a bulbous protrusion out of the plane of the circumference of the stent. The methods and apparatus of the present invention are illustratively described with respect to the low-mass, unitary mesh-like stent structure described in U.S. Pat. No. 4,733,665. It will of course be understood that the present invention is not limited to that stent structure, but is generally applicable to previously known stents such as those described above to reduce the potential for vessel abrasion and dissection during delivery.

Figure 1:
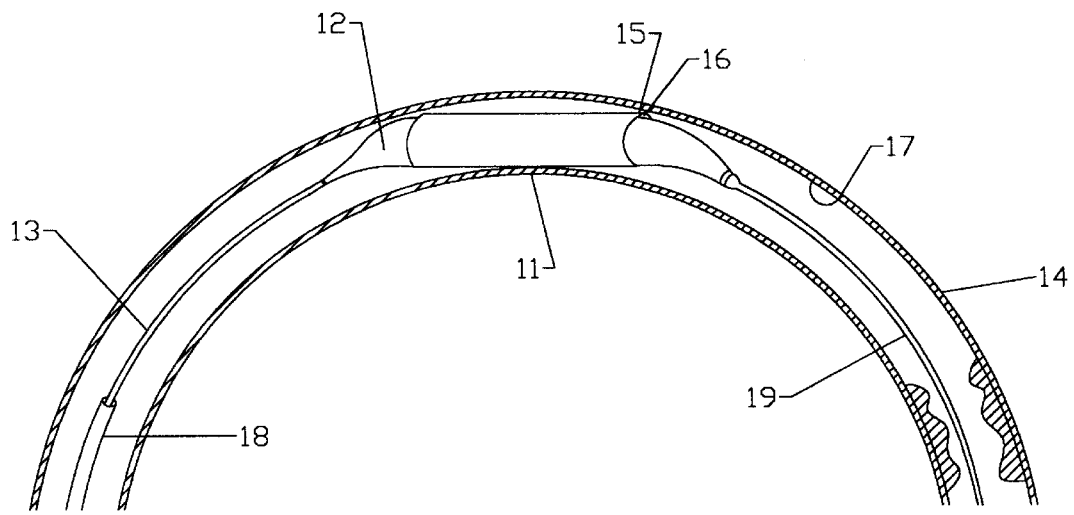
FIG. 1 is an elevational sectional view of an illustrative prior art stent attempting to negotiate a curve in a narrow vessel.

FIG. 1 is a diagrammatic side view of prior art stent 11 shown compressed on a delivery device, in this case on balloon 12 of balloon catheter 13. Stent 11 is shown attempting to negotiate a curve while passing through the lumen of narrow vessel 14. Distal end 15 of substantially rigid stent 11 separates from the pliable balloon material and flexible catheter 13 as catheter 13 and balloon 12 curve to follow the contour of the vessel 14. The separation is illustratively shown as gap 16. Distal end 15 contacts intima 17 of vessel 14 because substantially rigid metallic stent 11 does not bend around the curve in the vessel wall as readily as flexible catheter 13 and pliable balloon 12. Depending upon the condition of vessel 14, contact by distal end 15 of stent 11 may cause abrasion to intima 17, or even dissection of vessel 14. More important, it may be impossible to deliver stent 11 to the desired location in vessel 14 if stent 11 cannot be maneuvered through the turn.

Figure 3A:
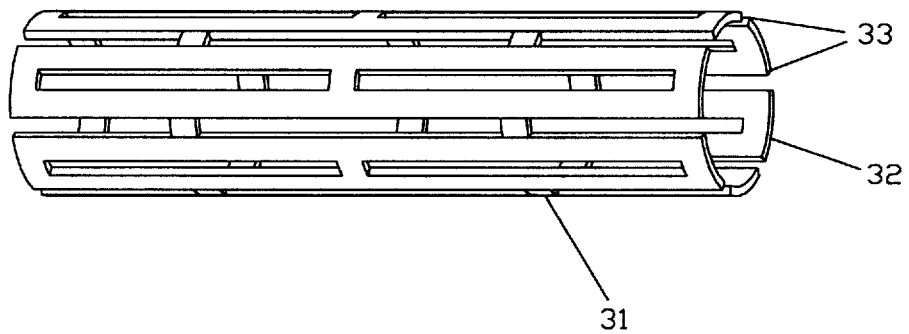
FIGS. 3A–3B show respectively, perspective and end views of an illustrative prior art mesh stent.
Figure 3B:
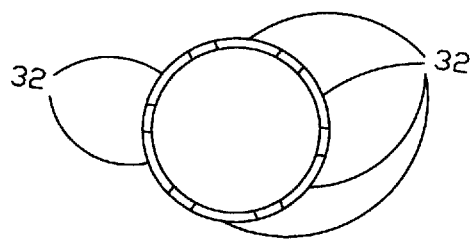

FIGS. 3A–3B show views of a typical mesh stent 31 such as described in Palmaz U.S. Pat. No. 4,733,665. FIG. 3A is a perspective view of the entire stent while FIG. 3B shows an end view of the stent. In FIG. 3A the apices 32 of the stent are shown having right-angled corners 33. It is believed that the sharpness of these corners in combination with the thin profile of the flat end of the apices 32 contribute to the poor trackability of this stent when used without a sheath. In FIG. 3B the small profile presented by the apices 32 of the stent 31 to the vessel wall is readily observed. The thickness of the stent material in such stents is typically less than 0.005 inches.

Figure 2:
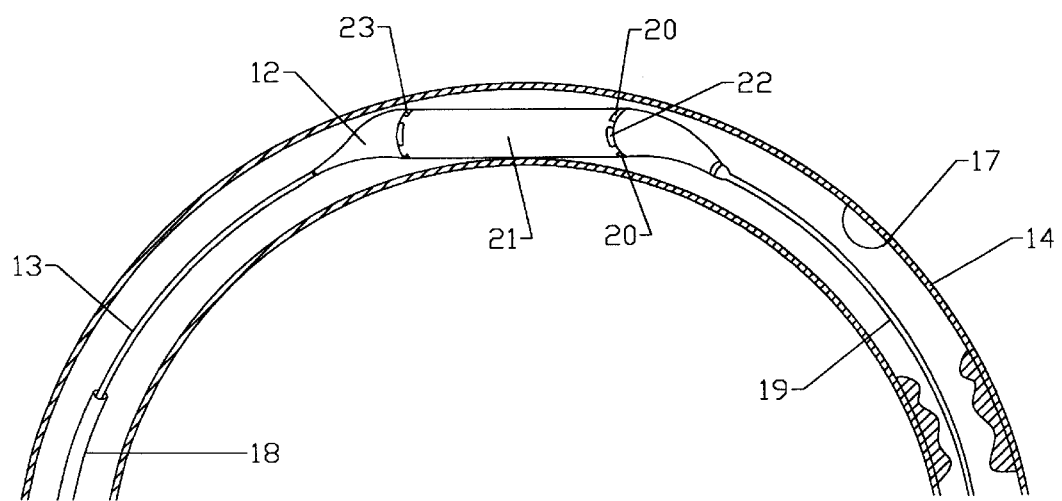
FIG. 2 is an elevational sectional view of an illustrative stent according to the present invention attempting to negotiate a curve in a narrow vessel.

Referring now to FIG. 2 which is illustrative of a stent 21 embodying the principles of the present invention as described. Items common with FIG. 1 are numbered identically with those of FIG. 1. Distal end 22 and proximal end 23 of stent 21 are provided with a radiused or bulbous portion 20 that protrudes beyond the outer circumference of the stent to increase the surface area of ends 22, 23. Bulbous portion 20 eliminates any sharp edges in the formation of stent 21 which may be formed of thin material. As stent 21 negotiates a curve, the curved surface reduces the risk that the ends of stent 21 will penetrate vessel 14.

Referring now to FIGS. 4A–4B, 5A–5B, radiused portions formed by several methods are shown. It is apparent from these figures that the apex of the stents of the present invention presents a larger radius profile to the wall of the vessel than does the apex of the prior art device shown in FIGS. 3A and 3B.

Figure 4A:
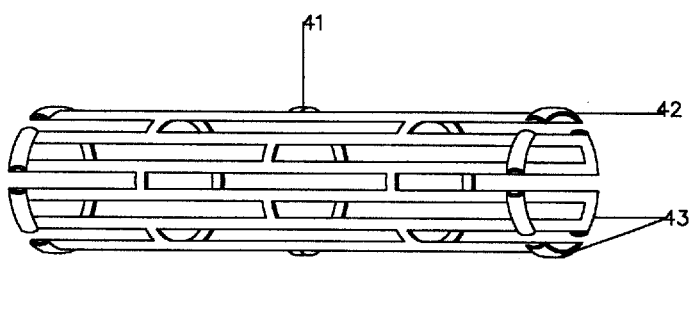
FIGS. 4A–4B show respectively, perspective and end views of an illustrative mesh stent constructed in accordance with the present invention and having bulbous portions created by bending the material of the stent wall at the apices of the stent outward.
Figure 4B:
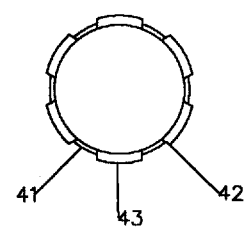

Stent 41 of FIGS. 4A–4B is formed by bending outward the stent material in the region of apex 42 of the stent. As shown in FIG. 4B the bending of the stent material adds radius 43 to the apex 42 of stent 41. As shown in FIG. 4B the bending of the stent material increases the profile of apex 42 that is presented to the wall of the vessel, thus reducing risk of injury or dissection.

Figure 5A:
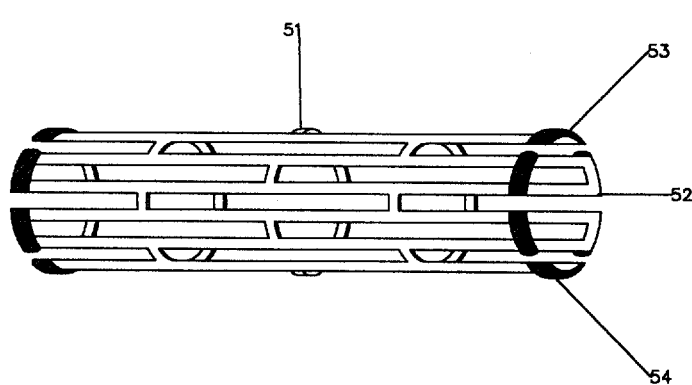
FIGS. 5A–5B show respectively, perspective and end views of an illustrative mesh stent constructed in accordance with the present invention and having bulbous portions created by providing extra material at the apices of the stent.
Figure 5B:
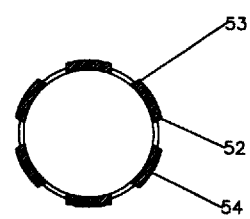

Stent 51 of FIGS. 5A–5B is formed by adding material 54 in the region of apex 52 of the stent. As shown in FIG. 5B the additional material adds radius 53 to the apex 52 of stent 51. As shown in FIG. 5B the additional material increases the profile of apex 52 that is presented to the wall of the vessel, thus reducing risk of injury or dissection.

The material 54 added in the region of the apex may have the same composition as the material of the stent or alternatively may have a different composition. For example the added material may be a metal or a non-metal. Metal material may be added to the radius in molten or powdered form and solidified around the apex using conventional metallurgical and soldering techniques. In addition, the radiused or bulbous portion may then be polished if desired to eliminate any irregularities.

A polymer material may also be formed around the apex of the stent in powdered or molten form. Alternatively, heat-shrink plastic elements may be inserted over portions of the stent and heat treated at the apex locations. Where a polymer is chosen to create the radiused portion, a suitable biocompatible polymer may be chosen which forms a good bond with the vessel over time. This integration of the ends of the stent with the intima of the vessel wall is expected to have the additional benefit of anchoring the stent over time.

The additional material at the apex of stent 51 in the region of apex 52 may also be provided by thickening the stent. For example, the apex of a stent such as stent 31 of FIG. 3A may be heated to form a bead of softened or molten stent material which forms the radius when cooled as, illustrated by stent 51 of FIG. 5A. The radius 53 may then be polished if desired to eliminate any irregularities. The thicker stent material adds radius 53 to apex 52 of stent 51. This additional thickness of the material increases the profile of apex 52 of stent 51 that is presented to the wall of the vessel as described hereinabove. It will be recognized by those skilled in the art that the increased thickness of material forming the radius at an apex of stent 51 also may be provided by using powder metallurgy techniques or selective machining.

Figure 6:
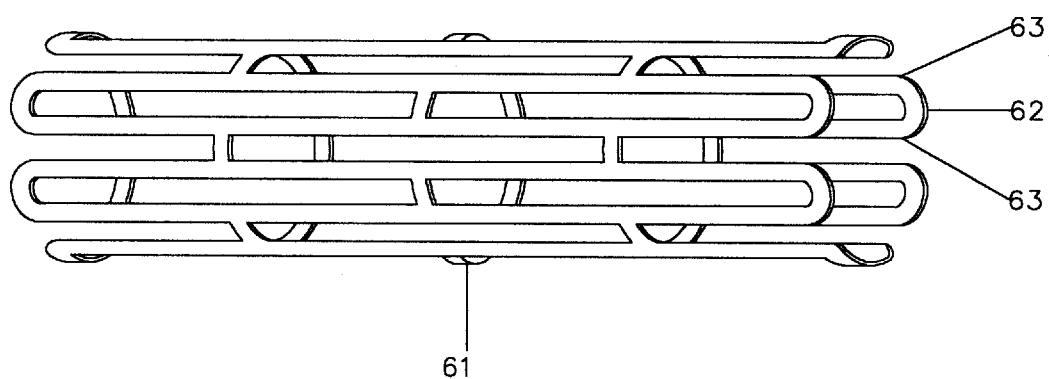
FIG. 6 shows a perspective view of an illustrative mesh stent constructed in accordance with the present invention and having a radius formed at the apices of the stent in the plane of the wall of the stent.

Stent 61 of FIG. 6 illustrates an alternative embodiment of the present invention in which the apex of the stent is provided with a radius in the plane of the wall of the stent. The apices 62 of stent 61 are rounded off at the edges 63. It is believed that while not necessarily increasing the thickness of stent 61 in the region of apices 62 of the stent, the radius provided by rounding the apices of the stent will improve trackability of the stent. The profile of the stent may additionally be increased by forming another radius on the stent by adding material in the region of the apices 62 as shown in FIGS. 5A and 5B.

Figure 7A:
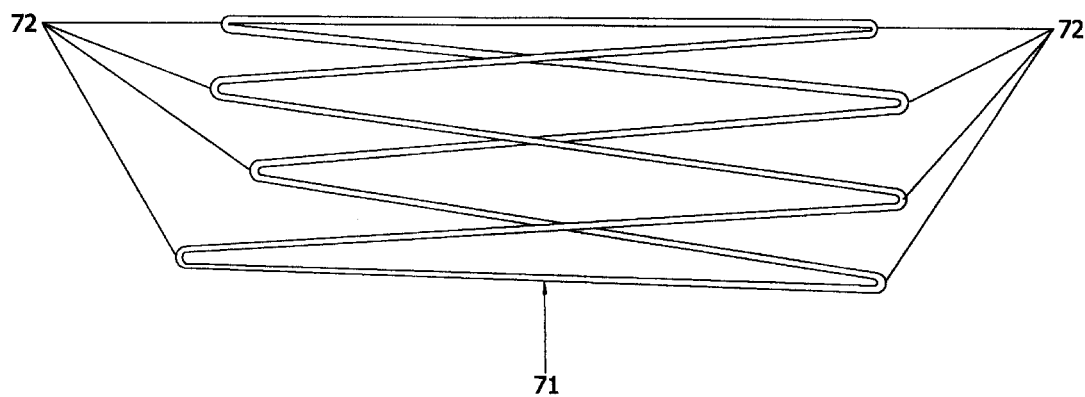
FIGS. 7A–7C show respectively, a prior art expandable wire-type stent, and two alternative embodiments of a stent similar to the stent of FIG. 7A but which additionally incorporate features of the present invention.
Figure 7B:
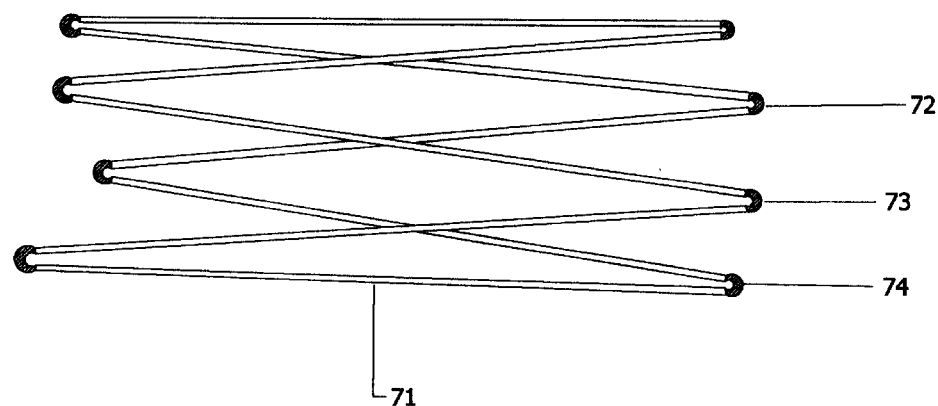
Figure 7C:
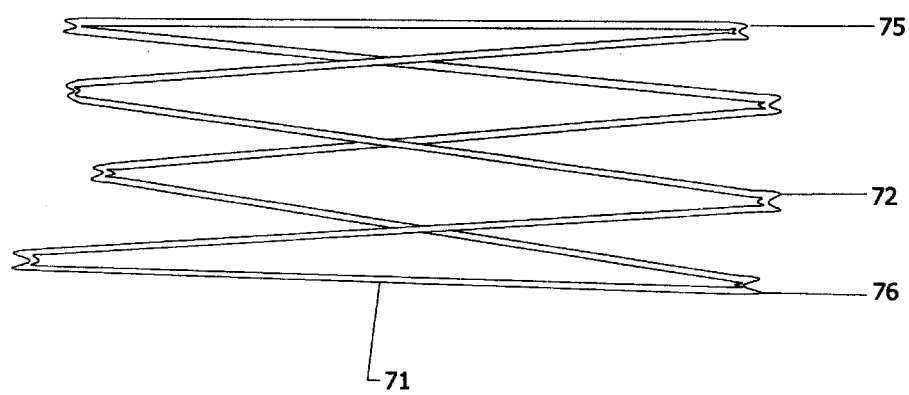

The stent of FIGS. 7A–7C is illustratively formed from a wire structure for example, like the stent described in Boneau U.S. Pat. No. 5,292,331. Such wire-type stents can be manufactured either by bonding together separate elements into the desired configuration or by bending a unitary piece of wire-like material. According to the present invention, a radiused portion can be provided on such stents by adding material or thickening the wire-like material at the apices of the stent as described above with respect to FIGS. 5A–5B. Referring to FIG. 7B the additional material 73 adds a radius 74 to stent 72 that increases the profile of apex 72 of stent 71. Stent 71 of FIG. 7C is formed by providing a twist 75 in the wire in the region of apex 72 of the stent to form radiused portion 76. The bending of the apex adds radius 76 to the stent 71. The radius increases the profile of apex 72 of stent 71, as described hereinabove.

The present invention provides further advantages during deployment, as described hereinabove. The stent and radii are preferably formed from radiopaque materials. Since there typically is more material in the end regions of the stents of the present invention compared to the stents of the prior art, the increased amount of radiopaque material at the ends of the stent are more clearly outlined during deployment, thereby assisting accurate placement of the stent.

While one application for the above-described stent includes treatment of cardiovascular disease such as atherosclerosis or other forms of coronary narrowing, the present invention may also be used for treatment of narrowed vessels in other components of the vascular system, for example, the kidney, leg, carotid artery, or elsewhere in the body. As will of course be appreciated, the size of the stent, as well as its external characteristics, may need to be adjusted to compensate for the differing sizes of the vessel to be treated.

While this invention has been described in connection with an illustrative preferred embodiment thereof, modifications and changes may be made thereto by those skilled in the art without departing from the spirit and scope of the invention. Accordingly, the scope of this invention is to be limited only by the appended claims.

What is claimed is:

1. In a stent having first and second ends and a wall surface disposed between the first and second ends and having a first diameter that permits intraluminal delivery and a second expanded diameter wherein the stent supports a lumen of a body passageway, the improvement comprising:
   a radiused or bulbous region disposed on the first end of the stent in a plane transverse to the stent;
   the radiused or bulbous portion increasing the profile of the stent in the region of the first end, to reduce the risk of injury to the lumen of the body passageway during introduction of the stent.

2. The stent as defined in claim 1 wherein the second end is provided with a radiused or bulbous portion.

3. The stent as defined in claim 1 wherein the radiused or bulbous portion is formed by adding material to the first end out of the plane of a circumference of the stent.

4. The stent as defined in claim 3 wherein the material has a different composition than the stent.

5. The stent as defined in claim 1 wherein the radiused or bulbous portion is formed by thickening the first end of the stent.

6. The stent as defined in claim 5 wherein the radiused or bulbous portion is formed by a step of heating the first end of the stent.

7. The stent as defined in claim 6 wherein the step of heating the first end of the stent is accomplished using a laser.

8. The stent as defined in claim 1 wherein the radiused or bulbous portion is formed by bending the wall of the stent at the first end.

9. In a stent for implantation within a lumen of a vessel within the human body comprising a plurality of N substantially straight segments of wire-like material, each segment having first and second ends, the first end of the first segment being connected to the first end of the second segment at a first apex, the second end of the second segment being connected to the second end of the third segment at a second apex, and so on until the second end of the Nth segment is connected to the second end of the first segment at the Nth apex, the improvement comprising:
   a radiused or bulbous portion disposed on each odd-numbered apex and increasing the profile of the apex to reduce the risk of injury to the lumen of the body passageway during introduction of the stent.

10. The stent as defined in claim 9 wherein each even-numbered apex is provided with a radiused or bulbous portion.

11. The stent as defined in claim 9 wherein the radiused or bulbous portion is formed by adding material to each odd-numbered apex out of the plane of a circumference of the stent.

12. The stent as defined in claim 11 wherein the material has a different composition than the stent.

13. The stent as defined in claim 9 wherein the radiused or bulbous portion is formed by thickening of the apex of the stent.

14. The stent as defined in claim 13 wherein the radiused or bulbous portion is formed by a step of heating the apex of the stent.

15. The stent as defined in claim 14 wherein the step of heating the stent is accomplished using a laser.

16. The stent as defined in claim 15 wherein the radiused or bulbous portion is formed by bending the odd numbered apices of the stent.

17. A method of manufacturing a stent comprising the steps of:

providing a tubular member having two ends and a plurality of apices at each end;

increasing the profile of a plurality of the apices so as to reduce the risk of injury to the lumen of the body passageway during introduction of the stent.

18. The method as defined in claim 17 wherein the step of increasing the profile of a plurality of the apices comprises the step of adding material to the apex out of the plane of a circumference of the stent.

19. The method as defined in claim 18 wherein the step of increasing the profile of a plurality of the apices comprises the step of adding a polymer material to the apex out of the plane of a circumference of the stent.

20. The method as defined in claim 17 wherein the step of increasing the profile of a plurality of the apices comprises the step of thickening an apex of the stent.

21. The method as defined in claim 20 wherein the step of thickening an apex of the stent comprises the step of heating an apex of the stent.

22. The method as defined in claim 21 wherein the step of heating an apex of the stent comprises the step of directing a laser at the apex of the stent.

23. The method as defined in claim 17 wherein the step of increasing the profile of a plurality of the apices comprises the step of twisting the apex of the stent out of the plane of a circumference of the stent.

* * * * *